(12) United States Patent
Barnes et al.

(10) Patent No.: US 8,154,810 B2
(45) Date of Patent: Apr. 10, 2012

(54) OPTICAL ASSEMBLIES FOR ADJUSTING WORKING DISTANCE AND FIELD OF VIEW IN AN IMAGING SYSTEM

(75) Inventors: Danny S. Barnes, Maple Valley, WA (US); Erik R. Stockinger, Seattle, WA (US); David P. Bajorins, Bothell, WA (US); Chace H. Fadlovich, Bothell, WA (US)

(73) Assignee: Microscan Systems, Inc., Renton, WA (US)

( * ) Notice: Subject to any disclaimer, the term of this patent is extended or adjusted under 35 U.S.C. 154(b) by 0 days.

(21) Appl. No.: 12/504,531

(22) Filed: Jul. 16, 2009

(65) Prior Publication Data

US 2011/0013297 A1 Jan. 20, 2011

(51) Int. Cl.
*G02B 7/02* (2006.01)
*G02B 3/12* (2006.01)
(52) U.S. Cl. ............... 359/823; 359/665; 359/666
(58) Field of Classification Search ........... 359/665, 359/823, 666, 672, 673, 674, 675, 819, 822, 359/827, 829, 66
See application file for complete search history.

(56) References Cited

U.S. PATENT DOCUMENTS

| | | | | |
|---|---|---|---|---|
| 5,739,959 | A * | 4/1998 | Quaglia | 359/666 |
| 7,782,548 | B2 * | 8/2010 | Yumiki et al. | 359/698 |
| 7,826,145 | B2 * | 11/2010 | Justis et al. | 359/666 |
| 7,826,146 | B2 * | 11/2010 | Campbell | 359/666 |
| 2002/0128710 | A1 * | 9/2002 | Eggleston | 623/6.22 |
| 2004/0066563 | A1 | 4/2004 | Voss et al. | |
| 2006/0056041 | A1 * | 3/2006 | Kato et al. | 359/665 |
| 2007/0097494 | A1 * | 5/2007 | Tokuda et al. | 359/368 |
| 2008/0084532 | A1 * | 4/2008 | Kurtin | 351/57 |
| 2008/0158678 | A1 | 7/2008 | Costigan et al. | |
| 2008/0285143 | A1 * | 11/2008 | Batchko et al. | 359/665 |
| 2009/0021823 | A1 | 1/2009 | Heim et al. | |
| 2010/0276492 | A1 * | 11/2010 | Wang et al. | 235/470 |

OTHER PUBLICATIONS

PCT/US2010/039549, International Search Report and Written Opinion of the International Searching Authority, mail date Jan. 25, 2011, 7 pages.

* cited by examiner

*Primary Examiner* — Mohammed Hasan
(74) *Attorney, Agent, or Firm* — Blakely Sokoloff Taylor & Zafman LLP (57) ABSTRACT

Embodiments of an apparatus comprising a base including a proximal end, a distal end, and a receptacle in the distal end that is adapted to interchangeably receive a lens adapter; a set of base optics positioned in the proximal end of the base; and adjustable-focus optics positioned in the base and optically coupled to the base optics and, when the lens adapter is present, to the lens adapter. Embodiments of a process including forming a base including a proximal end, a distal end, and a receptacle in the distal end that is adapted to interchangeably receive any one of a plurality of lens adapters; positioning a set of base optics in the proximal end of the base; and positioning adjustable-focus optics positioned in the base such that they are optically coupled to the base optics and, when the lens adapter is present, to the lens adapter. Other embodiments are disclosed and claimed.

29 Claims, 7 Drawing Sheets

OPTICAL ASSEMBLIES FOR ADJUSTING WORKING DISTANCE AND FIELD OF VIEW IN AN IMAGING SYSTEM

TECHNICAL FIELD

The present invention relates generally to imaging system optics and in particular, but not exclusively, to interchangeable and adaptable optics for adjusting working distance and field of view in an imaging system.

BACKGROUND

Optical data-reading systems have become an important and ubiquitous tool in tracking many different types of items, and machine-vision systems have become an important tool for tasks such as part identification and inspection. Both optical data-reading systems and machine vision systems capture a two-dimensional digital image of an optical symbol (in the case of an optical data-reading system) or a part to be inspected or analyzed (in the case of a general machine-vision system) and then proceed to analyze that image to extract the information contained in the image. One difficulty that has emerged in both types of systems is that of ensuring that the optics used to capture images have the correct field of view, depth of field and working focal distance for the application in which they are or will be used. Without optics having the correct characteristics for an application, it can be difficult or impossible for the system to capture images that can be analyzed.

In some cases, a customer that buys an imaging system doesn't know ahead of time what the required field of view, depth of field and working focal distance will be. In other cases, the customers' requirements are such that the field of view, depth of field and working focal distance are highly variable. In either case, with imaging systems having fixed-focus optics the customer would be forced to buy multiple systems to be able to fit one to their need. Imaging systems with zoom lenses have emerged as one solution, but these have drawbacks as well. A given zoom lens may not have the needed combination of field of view, depth of field and working focal distance. Zoom lenses are also complex, expensive, and have many moving parts that generate debris that can contaminate elements within the imaging system, such as the image sensor, and can lead to decreased system performance.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE ILLUSTRATED EMBODIMENTS

Embodiments of an apparatus, system and method for adjusting working focal distance, depth of field and field of view in an imaging system using interchangeable and adaptable optical assemblies are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
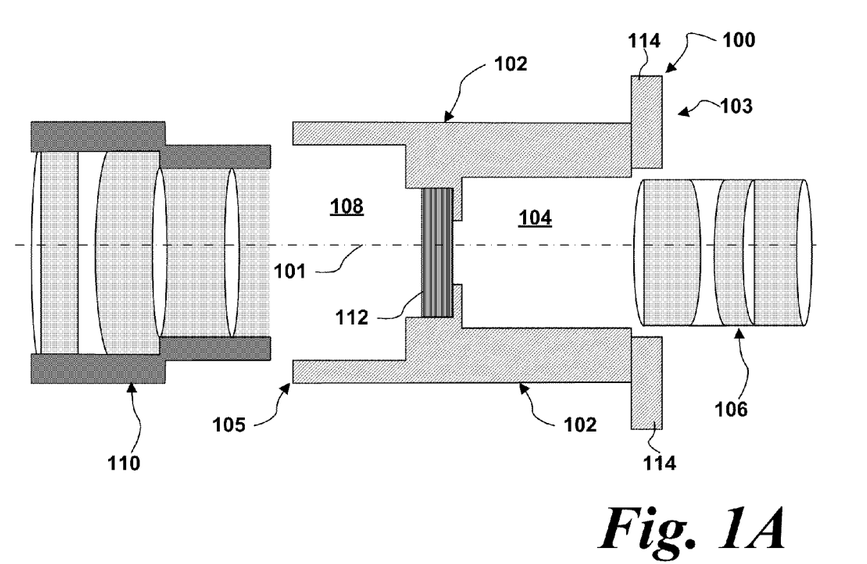
FIG. 1A is an exploded sectional view of an embodiment of an optical assembly.
Figure 1B:
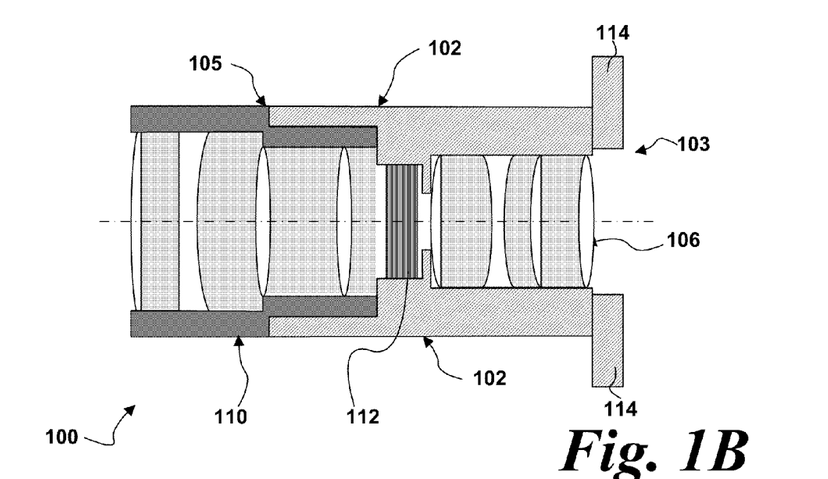
FIG. 1B is an assembled sectional view of the embodiment of an optical assembly shown in FIG. 1A.

FIGS. 1A and 1B illustrate an embodiment of an optical assembly 100 with interchangeable and adaptable components that allow adjustment of the field of view, depth of field and working focal distance of optical assembly 100. FIG. 1A is an exploded view of optical assembly 100, while FIG. 1B shows the optical assembly in its assembled state. In the illustrated embodiment, optical assembly 100 is axisymmetric about centerline/optical axis 101, but in other embodiments it need not be axisymmetric about its optical axis. Optical assembly 100 includes a base 102 having a proximal end 103 and a distal end 105. A mount 114 is positioned at the proximal end 103 to allow optical assembly 100 to be mounted to an image sensor (see FIG. 7). A receptacle 104 is formed in proximal end 103 and is sized and shaped to receive base optics 106. Base optics 106 can be positioned in receptacle 104 and secured therein. In one embodiment base optics 106 can be permanently mounted in receptacle 104, but in other embodiments base optics 106 can be interchanged by a user of optical assembly 100. In still other embodiments, base optics 106 can be an integral part of base 102.

Another receptacle 108 is formed in distal end 105 and is sized and shaped to interchangeably receive a lens adapter 110 such that it is positioned along optical axis 101 and optically coupled to adjustable-focus optics 112 and base optics 106. Lens adapter 110 is interchangeable, meaning that the lens adapter can be inserted in receptacle 108, secured in the receptacle, unsecured from the receptacle and removed from receptacle 108 at any time by a user of optical assembly 100 without damaging or disassembling optical assembly 100. A series of lens adapters 110 having different combinations of working focal distance, field of view and depth of field can be designed to fit within receptacle 108, so that the optical properties of optical assembly 100 can be changed at any time by the user simply by swapping the current lens adapter for a different lens adapter that has the desired combination of optical characteristics.

Optical assembly 100 also includes adjustable-focus optics 112. Adjustable-focus optics 112 are positioned within base 102 such that they are in the optical path between lens adapter 110 and base optics 106, in this embodiment meaning that they are positioned along centerline/optical axis 101. Adjustable-focus optics 112 are thus optically coupled to both lens adapter 110 and base optics 106 and serve to optically couple lens adapter 110 to base optics 106. Adjustable-focus optics 110 allow optical assembly 100 to adapt to different lens adapters 110 that can be used with optical assembly 100.

Figure 2:
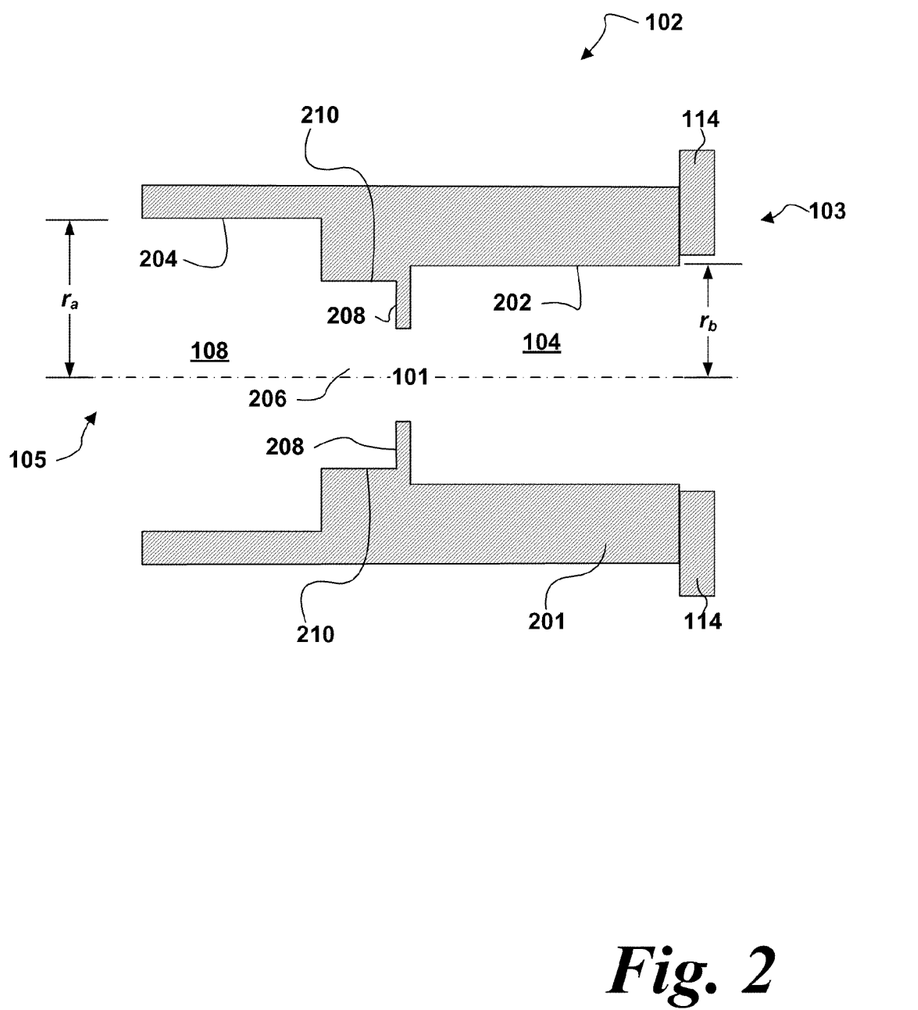
FIG. 2 is a sectional view of an embodiment of a base that can be used in embodiments of an optical assembly such as the one shown in FIGS. 1A-1B.

FIG. 2 illustrates the details of an embodiment of base 102. Base 102 includes a housing 201 designed to accommodate the other components of optical assembly 100 and a mount 114 to allow base 102, as well as other components of optical assembly 100, to be coupled to an image sensor (see FIG. 7). In the illustrated embodiment housing 201 is axisymmetric about centerline/optical axis 101, but in other embodiments it need not be axisymmetric. In one embodiment base 102 can be made of metal, but in other embodiments other materials such as plastics can be used. Base 102 can be a single piece in an embodiment, for example where it is machined from a block of metal, but in other embodiments it can include several pieces that are assembled.

Base 102 includes a receptacle 108 in distal end 105 that is designed to accommodate at least part of a lens adapter 110. In an axisymmetric embodiment of housing 201, receptacle 108 will be a substantially cylindrical cavity with a radius $r_a$ that approximately corresponds to the radius $r_a$ of the particular lens adapter used (see FIGS. 6A-6B), but in other embodiments the shape and size of receptacle 108 need not match the shape and size of adjustable-lens adapter 110, provided that adequate provisions can be made to secure the lens adapter within the receptacle. The cavity that forms receptacle 108 is bounded around its perimeter by interior surface 204 of housing 201. The exact nature of interior surface 204 will depend on the particular lens adapter 110 used and the provisions made for securing the lens adapter in the receptacle. For instance, in an embodiment in which lens adapter 110 is threaded (see FIG. 6A), interior surface 204 can include complementary threads to receive the threads on the portion of lens adapter 110 that is inserted in receptacle or cavity 108. In other embodiments where lens adapter is secured differently, interior surface 204 can be different (see, e.g., FIG. 6B).

Receptacle 104 is formed in proximal end 103 and is designed to accommodate base optics 106. In an embodiment in which base optics 106 are axisymmetric receptacle 104 can be an axisymmetric cavity, for instance a substantially cylindrical cavity with a radius $r_b$ that approximately corresponds to the radius $r_b$ of the particular base optics used (see FIG. 5). In still other embodiments the shape and size of receptacle 104 need not match the shape and size of base optics 106, provided that adequate provisions can be made to secure base optics 106 within the receptacle. Receptacle or cavity 108 is bounded around its perimeter by interior surface 202 and flange 208. Similarly to interior surface 204, the exact nature of interior surface 202 will depend on the particular base optics used and the provisions made for securing the base optics in the receptacle.

Receptacle 206 is positioned within housing 201 between receptacle 104 and receptacle 108 to accommodate adjustable-focus optics 112. Receptacle 206 comprises a cavity whose shape and size will depend on the particular adjustable-focus optics that are used. In one embodiment the cavity that forms receptacle 206 can be axisymmetric, but in other embodiments it need not be. In still other embodiments the shape and size of receptacle 206 need not match the shape and size of adjustable-focus optics 112, provided that adequate provisions can be made to secure adjustable-focus optics 112 within the receptacle. The cavity that forms receptacle 206 is bounded by interior walls 210 and by flange 208 that projects from the sides of housing 201 toward centerline/optical axis 101. As with interior walls 204, the nature of interior walls 210 will depend on the particular adjustable-focus optics used and the provisions made for securing them in the cavity. Flange 208, in addition to separating adjustable-focus optics 112 from base optics 106, provides support for the adjustable-focus optics and also provide additional ways to secure the adjustable-focus optics within the cavity. In another embodiment, flange 208 can be used to form an optical aperture.

Figure 3A:
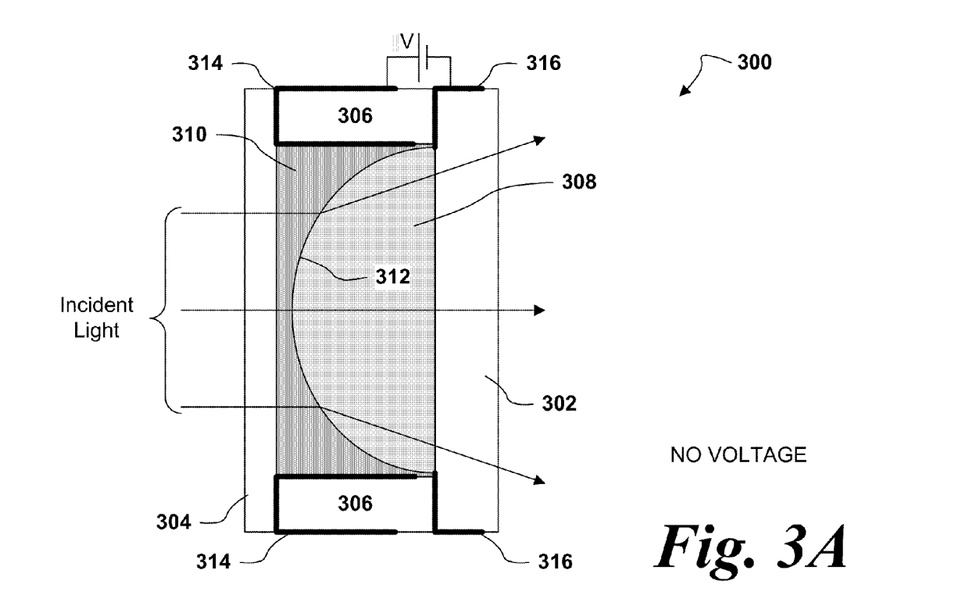
FIGS. 3A-3B are sectional views of an embodiment of adjustable-focus optics that can be used in embodiments of an optical assembly such as the one shown in FIGS. 1A-1B.
Figure 3B:
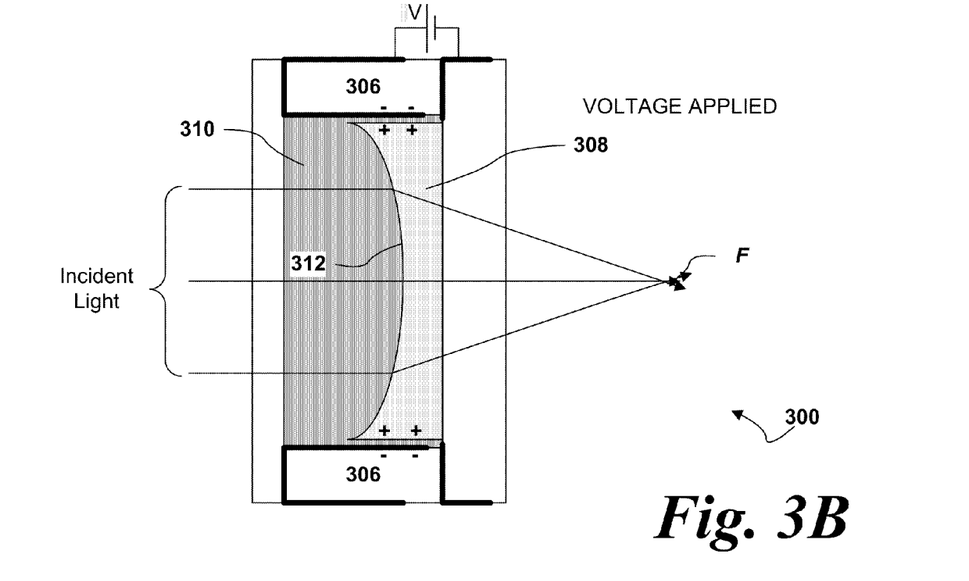

FIGS. 3A and 3B illustrate an embodiment of a liquid lens 300 that can be used as an embodiment of adjustable-focus optics 112 in optical assembly 100. FIG. 3A illustrates liquid lens 300 with no applied voltage, while FIG. 3B illustrates liquid lens 300 with an applied voltage. Other embodiments of a liquid lens, such as those manufactured and sold by Varioptic SA of France, can be also be used.

Liquid lens 300 includes substantially parallel spaced-apart covers 302 and 304. Covers 302 and 304 can be made of any optically transparent material; in one embodiment they can be made of glass, but in other embodiments other substances such as plastics can be used. Covers 302 and 304 can also include anti-reflective coatings. Spacers 306 are positioned at or near the edges of covers 302 and 304. Spacers 306 hold covers 302 and 304 apart and are sealed and attached to the two covers to create a hermetically sealed volume to hold two fluids 310 and 312. In one embodiment, spacers 306 are made of the same materials as covers 302 and 304, but in other embodiments other materials can be used. The hermetically sealed volume is lined with a hydrophobic coating.

Two fluids are contained within the hermetically sealed volume created by covers 302 and 304 and spacers 306. An electrically insulating fluid 310, such as an oil-based liquid, is placed in the hermetically sealed volume along with an electrically conducting fluid 308, such as a water-based liquid. A meniscus or boundary layer 312 is formed at the interface between electrically insulating fluid 310 and conducting fluid 308. Electrodes 314 are formed on spacer 306 and electrodes 316 are formed on cover 302, such that the electrodes extend into the interior of the hermetically sealed volume and are in electrical contact with one or both of insulating fluid 310 and conducting fluid 308. An adjustable and controllable voltage source V is electrically connected to electrodes 314 and 316.

In operation, when no voltage is applied to electrodes 314 and 316, water-based conducting fluid 308 is repelled by the hydrophobic coating on the interior of the hermetically sealed volume, causing the water-based conducting fluid 308 to be repelled by the coating and forcing the meniscus 312 between insulating fluid 310 and conducting fluid 308 into the shape shown in FIG. 3A, such that the conducting fluid 308 "beads" within the hermetically sealed volume and behaves as a concave divergent lens. When a voltage is applied to electrodes 314 and 316 the hydrophobic coating loses its hydrophobic properties and the surface tension between the two liquids drops, causing the insulating fluid 310 to relax and allowing conducting fluid 308 to touch the sides. As a result, meniscus 312 changes shape and flattens out to form a slight bulge in the opposite direction, making it a convex focusing lens the focuses incident light to a focal point F as shown in FIG. 3B. By controlling the voltage applied to electrodes 314 and 316, the exact shape of the meniscus, and thus the focusing power of liquid lens 300, can be precisely controlled. In other words, the exact position of focal point F can be controlled or, alternatively, the position of focal point F can be held substantially constant even if the nature of the incident light changes. By incorporating controlling the applied voltage, the focus of liquid lens 300 can be controlled automatically with an open-loop or closed-loop control system.

Figure 4A:
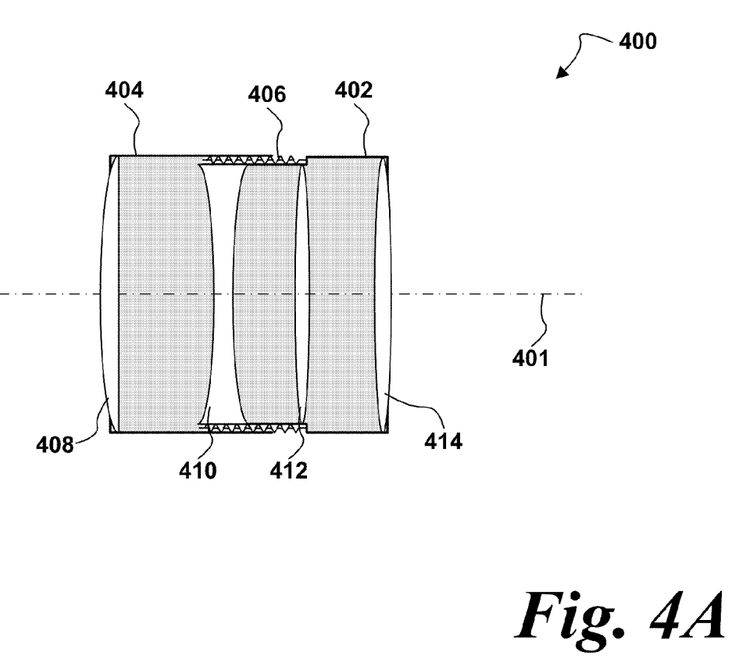
FIGS. 4A-4B are sectional views of alternative embodiments of adjustable-focus optics that can be used in embodiments of an optical assembly such as the one shown in FIGS. 1A-1B.

FIG. 4A illustrates an alternative embodiment of adjustable-focus optics 112 (see FIGS. 1A-1B). FIG. 4A illustrates adjustable-focus optics 400 that include a first section 402 and second section 404 aligned along optical axis 401. First section 402 and second section 404 are coupled to each other such that the two sections can translate relative to each other. In the embodiment shown the two sections are coupled by a threaded section 406, but in other embodiments they can be coupled by other means, such as tongue-and-groove. When put together, sections 402 and 404 form a housing within which optical elements are positioned and mounted. In the embodiment shown, optical elements within the housing include refractive lenses 408, 410, 412 and 414. In other embodiments, the optical elements within sections 402 and 404 can include a greater or lesser number of elements and can include other types of optical elements, such as compound refractive elements, reflective elements and diffractive elements. Still other embodiments can include some combination of two or more of refractive, reflective and diffractive elements. Further, although the illustrated embodiment has the optical elements 408-414 approximately regularly spaced, in other embodiments the spacing between optical elements can be irregular.

In adjustable-focus optics 400, lenses 410, 412 and 414 are positioned within first section 402, while lens 408 is positioned within second section 404. Thus, when second section 404 translates relative to first section 402, lens 408 changes position with respect to lenses 410, 412 and 414. As a result of the changing distances between lenses, the focus of adjustable-focus optics 400 is changed. In other embodiments, the distribution of optical elements between first section 402 and second section 404 can be different.

Figure 4B:
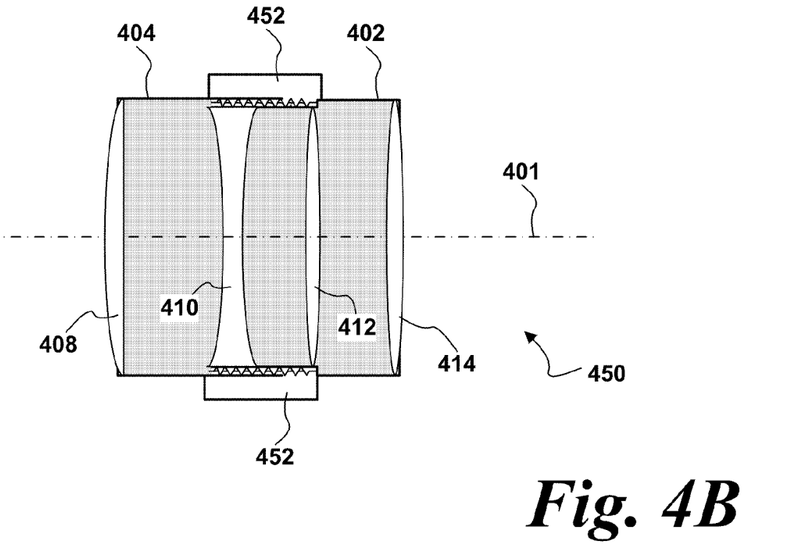

FIG. 4B illustrates another alternative embodiment of adjustable-focus optics 450. Adjustable-focus optics 450 are in most respects similar to adjustable-focus optics 400. The principal different between adjustable-focus optics 400 and adjustable-focus optics 450 is that optics 450 include a drive mechanism 452 coupled to first section 402 and second section 404 to translate the two sections relative to each other. In one embodiment drive mechanism 452 is an electric motor including mechanical elements such as gears and cams to translate the motion of an electric motor into linear motion between sections 402 and 404. In other embodiments, drive mechanism 452 can be something different, such as a solenoid drive. By incorporating a drive mechanism in the adjustable-focus optics, the focus of adjustable-focus optics 450 can be controlled automatically with an open-loop or closed-loop control system.

Figure 5:
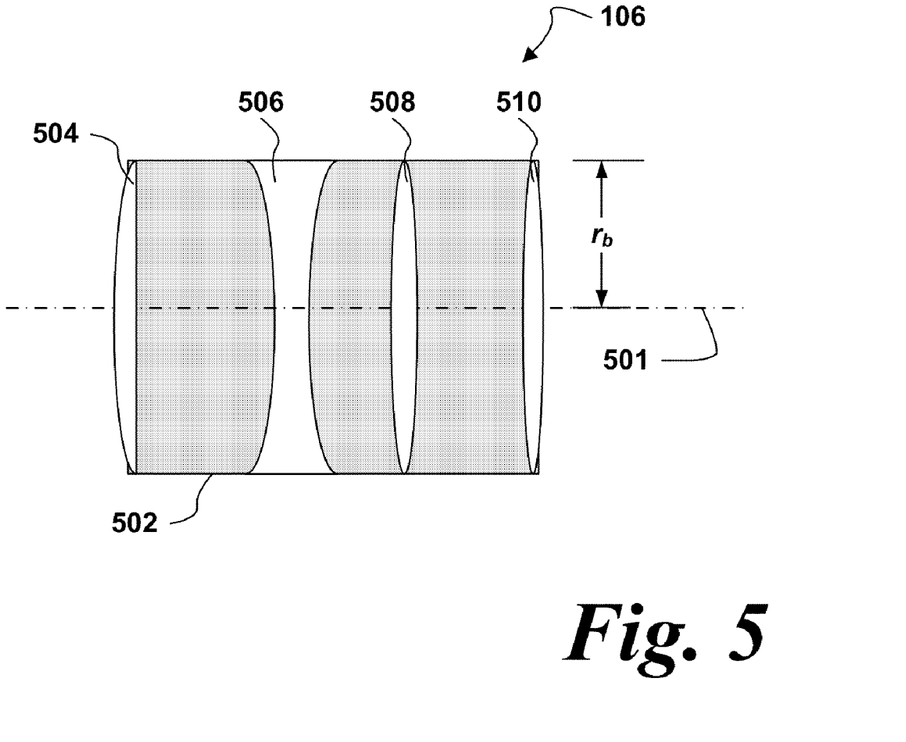
FIG. 5 is a sectional view of an embodiment of base optics that can be used in embodiments of an optical assembly such as the one shown in FIGS. 1A-1B.

FIG. 5 illustrates an embodiment of base optics 106. Base optics 106 include a housing 502 within which optical elements are positioned and mounted. Housing 502 is designed to fit in receptacle 104 (see FIG. 2), so in an embodiment of base 102 where receptacle 104 is axisymmetric with radius $r_b$, housing 502 can be axisymmetric and have a radius approximately equal to $r_b$ about optical axis 501. As discussed above, however, in some embodiments the shape and dimensions of receptacle 104 need not match the shape and dimensions of base optics 106. In other embodiments where base optics 106 are intended to be permanently mounted in base 102, however, housing 502 can be omitted and the optical elements can be installed directly in receptacle 104.

In the embodiment shown optical elements within the housing include refractive lenses 504, 506, 508 and 510, but in other embodiments the optical elements within housing 502 can include a greater or lesser number of elements and can include other types of optical elements, such as compound refractive elements, reflective elements and diffractive elements. Still other embodiments can include some combination of two or more of refractive, reflective and diffractive elements. Further, although the illustrated embodiment has the optical elements 504-510 approximately regularly spaced, in other embodiments the spacing between optical elements can be irregular.

Figure 6A:
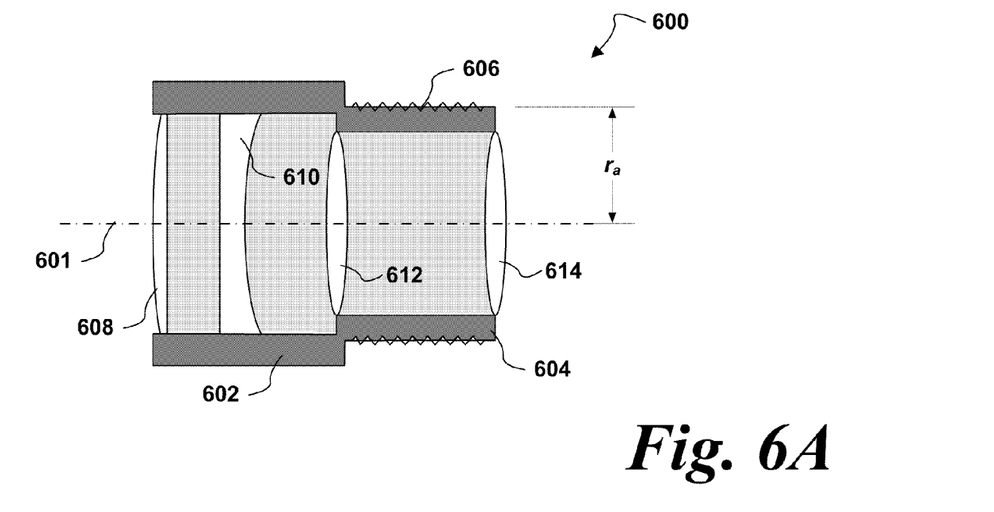
FIGS. 6A-6B illustrate embodiments of lens adapters that can be used in embodiments of an optical assembly such as the one shown in FIGS. 1A-1B.

FIG. 6A illustrates an embodiment of a lens adapter 600 that can be used as an embodiment of lens adapter 110 in optical assembly 100. Lens adapter 600 includes housing with a first section 602 and a second section 604. In the illustrated embodiment second section 604 is smaller than first section 602, but in other embodiments second section 604 can be the same size or larger than first section 602. In the illustrated embodiment first section 602 and second section 604 are axisymmetric about centerline/optical axis 601, but in other embodiments they need not be axisymmetric. In one embodiment lens adapter 600 can be made of metal, but in other embodiments other materials such as plastics can be used. Lens adapter 600 can be a single piece in on embodiment, for example where it is machined from a block of metal, but in other embodiments it can include several pieces that are assembled.

Second section 604 is design to fit within, and be secured within, receptacle 108 (see FIG. 2). In the illustrated embodiment second section 604 is axisymmetric and has a radius $r_a$ designed to approximately correspond to the radius $r_a$ of receptacle 108. As discussed above, in other embodiments lens adapter 600 need not be axisymmetric nor do its dimensions and shape need to match the dimensions and shape of receptacle 108, so long as the lens adapter can be optically aligned and securely held within receptacle 108. To secure lens adapter 600 in receptacle 108, second section 604 has a threaded outer surface 606 to mesh with corresponding threads on the inside surface 204 of receptacle 108, although other embodiments can use other ways of securing lens adapter 600 (see, e.g., FIG. 6B).

In the embodiment shown optical elements within the lens adapter 600 include refractive lenses 608, 610, 612 and 614, but in other embodiments the optical elements within lens adapter 600 can include a greater or lesser number of elements, and can include optical elements shaped differently than those shown. Moreover, other embodiments of lens adapter 600 can be made up of other types of optical elements such as compound refractive elements, reflective elements and diffractive elements. Still other embodiments can include some combination of two or more of refractive, reflective and diffractive elements. Further, although the illustrated embodiment has the optical elements 608-614 approximately regularly spaced, in other embodiments the spacing between optical elements can be irregular. The working focal length, field of view and depth of field of a given lens adapter 600 can be tailored by selecting appropriate optical elements.

Figure 6B:
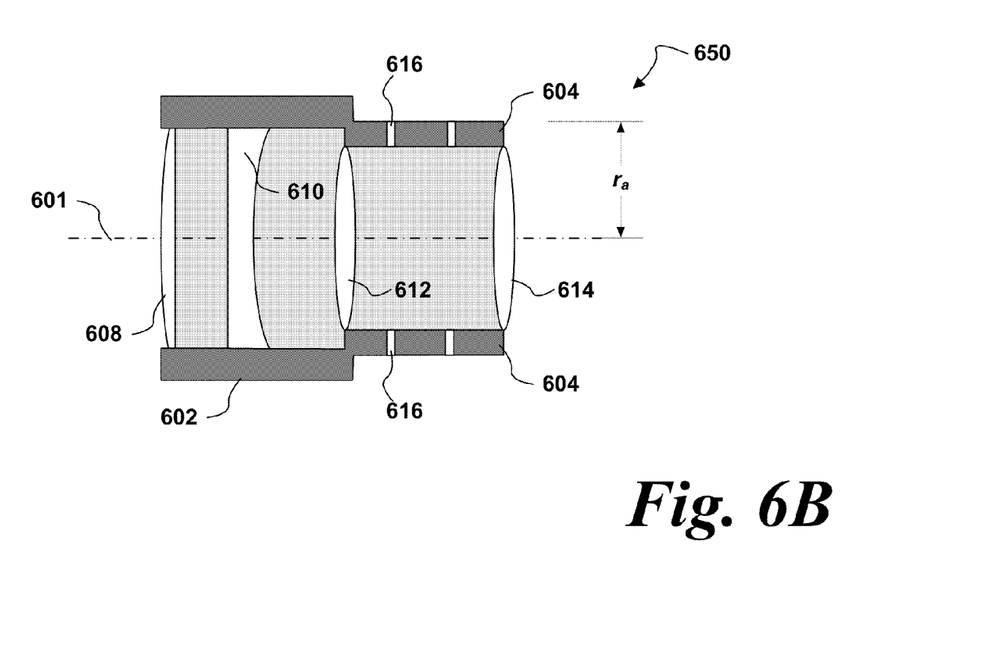

FIG. 6B illustrates an alternative embodiment of a lens adapter 650. Lens adapter 650 is in most respects similar to lens adapter 600. The principal different between the two is that lens adapter 650 includes different means for securing second section 604 within receptacle 108. In lens adapter 650, second section 604 is inserted into receptacle 108 and secured in place with pins or screws that extend through housing 201 (see FIG. 2) and into holes 616 in the walls of section 604.

Figure 7:
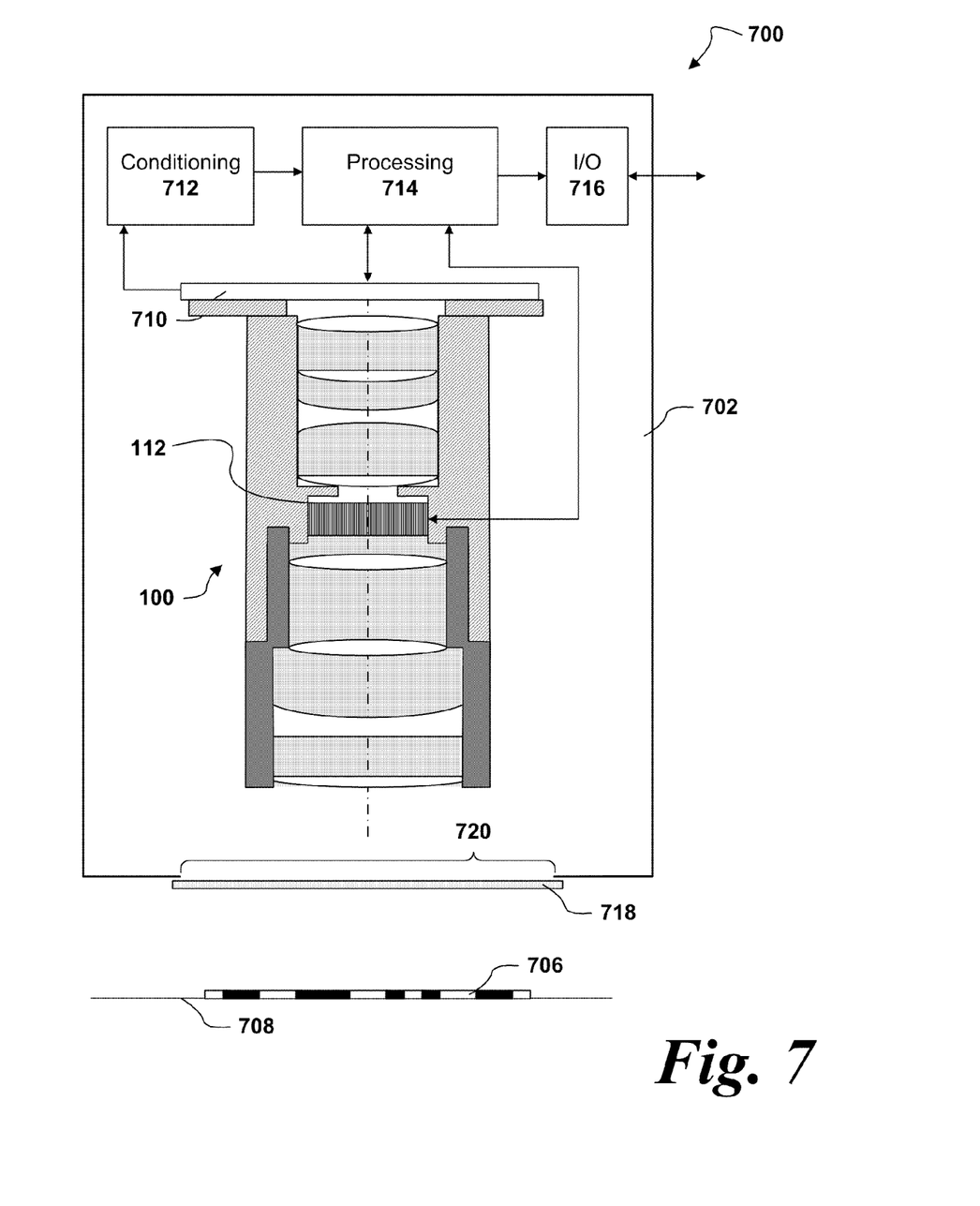
FIG. 7 illustrates an embodiment of an imaging system using embodiments of an optical assembly such as the one shown in FIGS. 1A-1B.

FIG. 7 illustrates an embodiment of an imaging system 700 that incorporates an embodiment of optical assembly 100. Imaging system 700 includes a housing 702 within which are positioned optical assembly 100 and image sensor 710. In addition to optical assembly 100 and image sensor 710, imaging system 700 includes a signal conditioner 712 coupled to image sensor 710; a processor 714 coupled to signal conditioner 712, image sensor 710 and adjustable-focus optics 112; and an input/output unit 716 coupled to processor 714. Although not shown, an internal or external power supply provides electrical power to the components within housing 702. In one embodiment, imaging system 700 can be a small portable handheld system, but in other embodiments it can be a fixed-mount imaging system. Optical assembly 100 and image sensor 710 are positioned within housing 702 such that opening 120 will face toward an object to be illuminated and imaged. In the illustrated embodiment, the object to be illuminated and imaged is an optical symbol such as a bar code or matrix code 706 on a surface 708, but in other embodiments the object can be a part or surface of a part that is subject to machine vision inspection.

Imaging system 700 includes a cover 718 over the bottom of the illuminator to prevent contaminants or other objects from entering the system through opening 720 and damaging the components in it. Although in the illustrated embodiment cover 718 is shown mounted to the exterior side of housing 702, in other embodiments cover 718 could be mounted to the inside or some other part of the housing. In one embodiment cover 718 is transparent and is very thin to avoid compromising the image, but in other embodiments the thickness of cover 718 can be greater or smaller. In some embodiments, cover 718 can include an anti-reflective coating on the inside, outside, or both the inside and the outside.

Image sensor 710 is coupled to optical assembly 100 and includes a two-dimensional pixel array. In one embodiment, image sensor 710 includes a CMOS image sensor, although in other embodiments different types of image sensors such as CCDs can be used. Image sensor 710 and optical assembly 100 are positioned within housing 702 such that optical assembly 100 is optically aligned with opening 720 in housing 702. Optically aligning optical assembly 100 with opening 720 allows optical assembly 100 to focus an image of object 706 onto image sensor 710, enabling image sensor 710 to capture an image of object 706.

Signal conditioner 712 is coupled to image sensor 710 to receive and condition signals from the pixel array in image sensor 710. In different embodiments, signal conditioner 712 can include various signal conditioning components such as filters, amplifiers, offset circuits, automatic gain control, analog-to-digital converters (ADCs), digital-to-analog converters, etc.

Processor 714 is coupled to signal conditioner 712 to receive conditioned signals corresponding to each pixel in the pixel array of image sensor 710. Processor 714 can also be coupled directly to image sensor 710 and to adjustable-focus optics 112, forming an open or closed-loop control system by which the processor can provide control signals that adjust elements within the image sensor 710 or adjust the focus of adjustable-focus optics 112. In a closed-loop control system, processor 714 can also receive signals from image sensor 710 and adjustable-focus optics 112 and use the information in these signals to control these elements. Processor 714 can include a processor and memory, as well as logic or instructions to process the image data to produce a final digital image and to analyze and decode the final image. In one embodiment, processor 714 can be a general-purpose processor, while in other embodiments it can be an application specific integrated circuit (ASIC) or a field-programmable gate array (FPGA).

Input/output circuit 716 is coupled to processor 714 to transmit the image and/or information decoded from the image to other components (not shown) that can store, display, further process, or otherwise use the image data or the decoded information. Among other things, input/output circuit 716 can include a processor, memory, storage, and hard-wired or wireless connections to one or more other computers, displays or other components.

In the illustrated embodiment, elements 712, 714 and 716 are shown co-housed with image sensor 701 and optical assembly 100, but in other embodiments, elements 712, 714 and 716 can be positioned outside housing 702. In still other embodiments one or more of elements 712, 714 and 716 can be integrated within image sensor 710.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
   a base including a proximal end, a distal end, and a receptacle in the distal end that is adapted to interchangeably receive a lens adapter;
   a set of base optics positioned in the proximal end of the base, the set of base optics including at least one optical element having optical power; and
   electrically activated, adjustable-focus optics positioned in the base and optically coupled to the base optics and, when the lens adapter is present, to the lens adapter, wherein the focal length of the adjustable-focus optics can be adjusted in a range that includes both positive and negative values.

2. The apparatus of claim 1 wherein the receptacle is threaded to receive a compatibly-threaded end of the lens adapter.

3. The apparatus of claim 1 wherein the base optics are interchangeable.

4. The apparatus of claim 1 wherein the base optics have a fixed focal length.

5. The apparatus of claim 1 wherein the adjustable-focus optics in the base comprises a liquid lens.

6. The apparatus of claim 5 wherein the liquid lens comprises two different liquids.

7. The apparatus of claim 1, further comprising a lens adapter positioned in the receptacle and optically coupled to the adjustable-focus optics.

8. The apparatus of claim 7 wherein the lens adapter is selected from among a plurality of lens adaptors having different combinations of field of view, depth of field, and working focal length.

9. The apparatus of claim 1, further comprising a mount on the proximal end of the base for mounting the apparatus to an image sensor.

10. A system comprising:
an optical assembly comprising:
a base including a proximal end, a distal end, and a receptacle in the distal end that is adapted to interchangeably receive a lens adapter,
a set of base optics positioned in the proximal end of the base, the set of base optics including at least one optical element having optical power,
electrically activated, adjustable-focus optics positioned in the base and optically coupled to the base optics and, when the lens adapter is present, to the lens adapter, wherein the focal length of the adjustable-focus optics can be adjusted in a range that includes both positive and negative values; and
an image sensor optically coupled to the optical assembly.

11. The system of claim 10 wherein the adjustable-focus optics in the base comprises a liquid lens.

12. The system of claim 11 wherein the liquid lens comprises two different liquids.

13. The system of claim 10, further comprising a lens adapter positioned in the receptacle and optically coupled to the adjustable-focus optics.

14. The system of claim 13 wherein the lens adapter is selected from among a plurality of lens adaptors having different combinations of field of view, depth of field, and working focal length.

15. The system of claim 10, further comprising a signal conditioning circuit coupled to the image sensor.

16. The system of claim 15, further comprising a processor coupled to the signal conditioning unit and to the image sensor.

17. The system of claim 16 wherein the processor is further coupled to the adjustable-focus optics.

18. The system of claim 16, further comprising an input/output unit coupled to the processor.

19. A process comprising:
forming a base including a proximal end, a distal end, and a receptacle in the distal end that is adapted to interchangeably receive any one of a plurality of lens adapters;
positioning a set of base optics in the proximal end of the base, the set of base optics including at least one optical element having optical power; and
positioning electrically activated, adjustable-focus optics in the base such that they are optically coupled to the base optics and, when one of the plurality of lens adapters is present, to the lens adapter, wherein the focal length of the adjustable-focus optics can be adjusted in a range that includes both positive and negative values.

20. The process of claim 19 wherein the receptacle is threaded to receive a compatibly-threaded end of the lens adapter.

21. The process of claim 19 wherein the base optics are interchangeable.

22. The process of claim 19 wherein the base optics have a fixed focal length.

23. The process of claim 19 wherein the adjustable-focus optics in the base comprises a liquid lens.

24. The process of claim 23 wherein the liquid lens comprises two different liquids.

25. The process of claim 19, further comprising positioning a lens adapter in the receptacle such that it is optically coupled to the adjustable-focus optics.

26. The process of claim 25 wherein the lens adapter is selected from among a plurality of lens adaptors having different combinations of field of view, depth of field, and working focal length.

27. The process of claim 19, further comprising forming a mount on the proximal end of the base for mounting the optical assembly to an image sensor.

28. The system of claim 10, further comprising an open-loop control system coupled to the adjustable-focus optics.

29. The system of claim 10, further comprising a closed-loop control system coupled to the image sensor and to the adjustable-focus optics.

* * * * *